United States Patent
Gill et al.

(10) Patent No.: US 7,917,214 B1
(45) Date of Patent: Mar. 29, 2011

(54) METHODS AND SYSTEMS FOR IDENTIFYING A PREFERRED PACING CONFIGURATION FOR A MULTI-ELECTRODE IMPLANTABLE CARDIAC ELECTROTHERAPY DEVICE

(75) Inventors: Jong Gill, Valencia, CA (US); Annapurna Karicherla, Valenica, CA (US); Kyungmoo Ryu, Palmdale, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 804 days.

(21) Appl. No.: 11/851,240

(22) Filed: Sep. 6, 2007

(51) Int. Cl.
*A61N 1/362* (2006.01)

(52) U.S. Cl. .............................................. 607/9; 607/27

(58) Field of Classification Search .......... 607/9, 26–28, 607/11–13
See application file for complete search history.

(56) References Cited

U.S. PATENT DOCUMENTS

| | | | |
|---|---|---|---|
| 5,466,254 A | 11/1995 | Helland | |
| 6,456,876 B1 * | 9/2002 | Kroll | 607/4 |
| 6,473,645 B1 | 10/2002 | Levine | |
| 6,477,417 B1 | 11/2002 | Levine | |
| 6,606,516 B2 | 8/2003 | Levine | |
| 6,909,916 B2 * | 6/2005 | Spinelli et al. | 607/9 |
| 6,978,178 B2 * | 12/2005 | Sommer et al. | 607/28 |
| 7,020,523 B1 * | 3/2006 | Lu et al. | 607/27 |
| 7,107,093 B2 | 9/2006 | Burnes | |
| 7,239,913 B2 | 7/2007 | Ding et al. | |
| 7,647,108 B2 * | 1/2010 | Freeberg | 607/28 |
| 2002/0151935 A1 | 10/2002 | Levine | |
| 2002/0193834 A1 | 12/2002 | Levine | |
| 2004/0102812 A1 | 5/2004 | Yonce et al. | |
| 2004/0106958 A1 | 6/2004 | Mathias et al. | |
| 2005/0038478 A1 * | 2/2005 | Klepfer et al. | 607/9 |
| 2009/0054946 A1 * | 2/2009 | Sommer et al. | 607/28 |

FOREIGN PATENT DOCUMENTS

WO 2006105474 A2 10/2006

OTHER PUBLICATIONS

Duytschaever, Mattias MD et al., "Methods for Determining the Refractory Period and Excitable Gap During Persistent Atrial Fibrillation in the Goat," Circulation. 2001;104:957-962.

Ogawa, Masahiro MD et al., "Novel Electrophysiologic Parameter of Dispersion of Atrial Repolarization: Comparison of Different Atrial Pacing Methods," J Cardiovasc Electrophysiol (Feb. 2002);13:110-117.

* cited by examiner

*Primary Examiner* — Carl H Layno
*Assistant Examiner* — Brian T Gedeon

(57) ABSTRACT

Methods and systems of identifying an electrode or combination of electrodes of a multi-electrode device for pacing include selecting a first electrode or electrode combination as a first candidate; delivering a pacing pulse through the first candidate and determining a measurement based on sensed cardiac electrical activity resulting from the first candidate pacing; selecting a second candidate; delivering a pacing pulse through the second candidate and determining a measurement based on sensed cardiac electrical activity resulting from the second candidate pacing; comparing the measurement for the first and second candidates; and identifying the first or second candidate for pacing based on the comparison. The measurement may be one or more of activation time $\Delta T_{act}$, activation recovery interval (ARI), a fractioned electrogram width, and a standard deviation of a fractioned electrogram feature.

6 Claims, 5 Drawing Sheets

Activation        End of Recovery

METHODS AND SYSTEMS FOR IDENTIFYING A PREFERRED PACING CONFIGURATION FOR A MULTI-ELECTRODE IMPLANTABLE CARDIAC ELECTROTHERAPY DEVICE

FIELD OF THE INVENTION

The present invention relates to medical devices and methods of using such devices. More specifically, the present invention relates to implantable cardiac electrotherapy devices and methods of using such devices.

BACKGROUND OF THE INVENTION

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease may be successfully treated by artificial cardiac pacing using implantable cardiac electrotherapy devices, including pacemakers and implantable defibrillators, which deliver rhythmic electrical pulses or other anti-arrhythmia therapies to the heart at a desired energy and rate. One or more heart chambers may be electrically stimulated depending on the location and severity of the conduction disorder.

Cardiac pacemakers conventionally stimulate a heart chamber by applying current pulses to cardiac tissues via two electrodes, a cathode and an anode. Standard pacing leads are available in either of two configurations, unipolar leads or bipolar leads, depending on the arrangement of the electrodes of a particular lead. A unipolar pacing lead contains a single electrode, normally the cathode, which extends pervenously distal from the pacemaker in an insulating enclosure until it is adjacent to the tip of the lead where the insulation is terminated to provide for electrical contact of the cathode with the heart tissue. The anode provides a return path for the pacing electrical circuit. For a unipolar lead, the anode is the pacemaker case.

A bipolar lead contains two electrodes within an insulating sheath, an anode that extends distal from the pacemaker to a position adjacent to, but spaced from, the electrode tip, and a cathode that also extends distal from the pacemaker, but terminates a short distance distal of the anode, at the lead tip. The anode commonly takes the form of a ring having greater surface area than the cathode tip. An insulating barrier separates the cathode and anode of a bipolar lead. In current pacemakers, circuits for pacing and sensing, which determine tip, ring and case electrode connections, are provided. Thus, the pacemakers may be programmed for either bipolar or unipolar operation with respect to either sensing or pacing operations.

Systems and methods have been developed for determining various operating conditions for implantable cardiac electrotherapy devices. For example, electrode configurations may be determined for sensing and stimulating, cathode and anode assignments may be determined, and coupling intervals may be determined for precisely controlling the activation sequence of electrodes. Determining such operating conditions may be particularly suitable for programmable control systems of implantable cardiac devices.

Although technology for implantable cardiac devices has advanced to provide multiple electrodes that are available for pacing and/or sensing, developing ways to take advantage of such technology is ongoing. It would be beneficial to be able to determine a preferred or optimal pacing configuration for a device implanted in a patient, for example, to provide an efficient electrotherapy and/or to provide an electrotherapy that is less likely to result in arrhythmia.

Thus, there is a need in the art for a system for identifying an electrode or combination of electrodes for a preferred or optimal pacing configuration for a multi-electrode implantable cardiac electrotherapy device. There is also a need in the art for a method of identifying an electrode or combination of electrodes for a preferred or optimal pacing configuration for a multi-electrode implantable cardiac electrotherapy device.

SUMMARY

The present invention contemplates identifying, selecting and/or using an electrode or combination of electrodes corresponding to a preferred or optimal pacing configuration. Specifically, embodiments of the invention contemplate using a conduction-based approach to identify, select and/or use an electrode or combination of electrodes for pacing. Such an approach may result in a fastest or optimal conduction across a region of cardiac tissue, resulting in an efficient application of electrotherapy. This may also provide improved contraction and/or hemodynamics.

The invention also contemplates using an activation recovery interval (ARI)-based approach to identify, select and/or use an electrode or combination of electrodes for pacing. Such an approach may result in a reduced vulnerability to developing arrhythmia from electrotherapy, resulting in a safer application of electrotherapy. Fractionated electrogram features may also be used to identify, select and/or use an electrode or combination of electrodes for pacing.

Embodiments of the invention also contemplate using a combined conduction-based and ARI-based approach to identify, select and/or use an electrode or combination of electrodes for pacing. Such an approach may allow a fastest or optimal conduction to be obtained without an undesirable or unacceptable susceptibility to arrhythmia. Such an approach may also provide systems and methods that are adaptable to a particular type of electrotherapy, such as resynchronization-type pacing or prevention-type pacing.

In general, the invention involves selecting a first electrode or combination of electrodes as a first candidate to be used for pacing and determining a measurement based on sensed cardiac electrical activity, for the first candidate. The invention further involves selecting a second electrode or combination of electrodes as a second candidate to be used for pacing and determining a measurement based on sensed cardiac electrical activity, for the second candidate. The measurements for the first and second candidates are compared and one of the first and second candidates is identified for pacing based on the comparison. As stated above, these measurements may be one or more of activation time $\Delta T_{act}$, activation recovery interval (ARI), a fractioned electrogram width, and a standard deviation of a fractioned electrogram feature While multiple embodiments are disclosed, still other embodiments of the present invention will become apparent to those skilled in the art from the following detailed description, which shows and describes illustrative embodiments of the invention. As will be realized, the invention is capable of

DETAILED DESCRIPTION

The following description relates to embodiments presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Embodiments of the present invention are described in relation to a cardiac stimulation device capable of delivering precisely ordered stimulation pulses to multiple chambers of the heart, referred to herein as multi-chamber stimulation, or to multiple sites within a chamber of the heart, referred to herein as multi-site stimulation. As used herein, the shape of the stimulation pulses is not limited to an exact square or rectangular shape, but may assume any one of a plurality of shapes that is adequate for the delivery of an energy packet or stimulus.

The stimulation device is intended for use in patients suffering from hemodynamic dysfunction, which may or may not be accompanied by conduction disorders. Precisely controlled stimulation at multiple sites or in multiple chambers is provided to intentionally make use of the pacing function of the heart to improve cardiac hemodynamics by re-coordinating heart chamber contractions and/or preventing arrhythmogenic depolarizations from occurring. Thus, the cardiac stimulation device is capable of delivering at least low-voltage stimulation pulses to multiple stimulation sites for providing pacing therapy, and may include high-voltage stimulation shocks for providing cardioversion therapy and defibrillation therapy.

Figure 1:
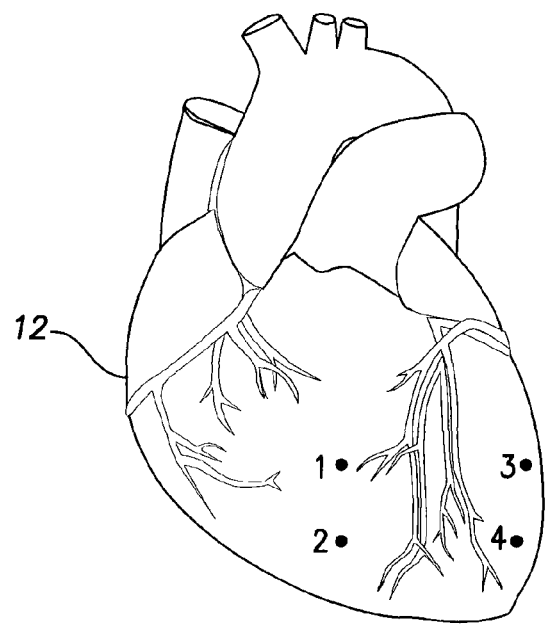
FIG. 1 is a diagrammatic illustration representing a plurality of epicardial electrodes of a cardiac stimulation device in electrical communication with a patient's heart.

FIG. 1 is a diagrammatic illustration representing a plurality of electrodes 1, 2, 3, 4 of a cardiac stimulation device (not shown) in electrical communication with a patient's heart 12. The electrodes 1, 2, 3, 4, in combination with the cardiac stimulation device, are configured to provide both pacing, i.e., delivery of electrical stimuli, and sensing, i.e., sensing of electrical cardiac activity. The electrodes 1, 2 are placed with respect to the right ventricle and the electrodes 3, 4 are placed with respect to the left ventricle. In one configuration, one or more the electrodes 1, 2, 3, 4 may be implanted in the intrapericardial space of the heart and placed on the heart's epicardial surface. In other configurations, as described further below, one or more of the electrodes 1, 2, 3, 4 may be placed with respect to the ventricles by an endocardial approach.

In one embodiment, the goal may be to identify, select and/or use one of the electrodes 1, 2, 3, 4 or a combination of two or more of the electrodes, i.e., candidate electrodes, for pacing such that a fastest conduction across the cardiac tissue is achieved. Fast conduction is likely to induce coherent and/or uniform contraction of the cardiac tissue, which may lead to improved hemodynamics. Thus, one embodiment provides a conduction-based approach for identifying an optimal pacing electrode or electrode combination.

Such an approach may selectively test individual candidates comprising one or more of the electrodes 1, 2, 3, 4 to determine an activation time $\Delta T_{act}$ for each candidate. The activation time $\Delta T_{act}$ for a particular candidate denotes the difference between the time of delivery of the pacing signal to cardiac tissue through the candidate electrode and the last (latest) activation sensed from one or more of the other, i.e., non-candidate, electrodes. The activation time $\Delta T_{act}$ for the candidate thus corresponds to the largest conduction time—of all measured conduction times—between the candidate electrode and the non-candidate electrodes.

For example, electrodes 1 and 3 may be selected as candidates for pacing. To determine the activation time $\Delta T_{act}$ for electrode 1, a pacing signal is applied to cardiac tissue through electrode 1 and activation times for each of the other electrodes 2, 3, 4 is determined based on the time that electrical cardiac activity is sensed at the electrode. The pacing signal is generated by a pulse generator of the cardiac stimulation device. The cardiac activations at each of the other electrodes 2, 3, 4 are sensed by either a bipolar or unipolar sensing configuration involving the electrode or in any known or hereafter developed manner, such as using one or more sensors capable of sensing an electrical impulse from each electrode 2, 3, 4.

Figure 2:
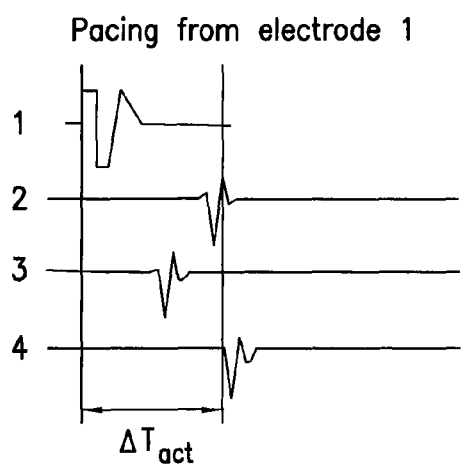
FIG. 2 illustrates an example of a conduction pattern representing a pacing stimulus delivered from the first electrode of FIG. 1 and corresponding cardiac activations sensed at the second, third and fourth electrodes.

FIG. 2 illustrates an example of a conduction pattern resulting from the delivery of a pacing stimulus through electrode 1. The cardiac activations sensed at each of the other electrodes 2, 3, 4 are illustrated. As shown, electrode 4 has the largest activation time. In other words, it was the last electrode "activated" by the pacing stimulus from the candidate electrode. Thus, the activation time $\Delta T_{act}$ for electrode 1 is measured from the time of the pacing signal at electrode 1 to the time cardiac activity is sensed at electrode 4.

Figure 3:
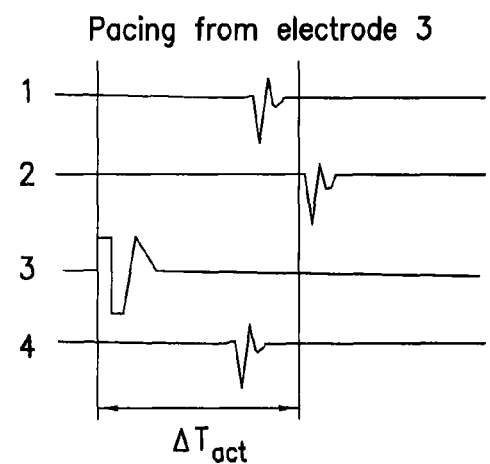
FIG. 3 illustrates an example of a conduction pattern representing a pacing stimulus delivered from the third electrode of FIG. 1 and corresponding cardiac activations sensed at the first, second and fourth electrodes.

Similarly, to determine the activation time $\Delta T_{act}$ for the other candidate, electrode 3, a pacing signal is applied through electrode 3 and the last "activation" of the other electrodes 1, 2, 4 is determined. FIG. 3 illustrates an example of a conduction pattern resulting from the delivery of a pacing stimulus through electrode 3. The cardiac activations sensed at each of the other electrodes 1, 2, 4 are illustrated. As shown, electrode 2 has the largest activation time. In other words, it was the last electrode "activated" by the pacing stimulus from the candidate electrode. Thus, the activation time $\Delta T_{act}$ for electrode 3 corresponds to the time between the pacing signal delivery at electrode 3 and the cardiac activation sensed at electrode 2.

A comparison is made between the activation times $\Delta T_{act}$ of the candidates. Based on the comparison, one of the candidates is identified as being preferred or optimal for pacing. In the examples of FIGS. 2 and 3, a comparison shows that the activation time $\Delta T_{act}$ for electrode 1 is shorter than the activation time $\Delta T_{act}$ for electrode 3. Thus, electrode 1 is identified as the preferred electrode for pacing stimulus delivery.

Although the foregoing description was in terms of single electrodes as candidates for pacing, it is understood that single electrodes and/or combinations of electrodes may be selected as candidates for pacing. For example, the present invention contemplates simultaneous multiple electrode pacing, as well as linear pacing from multiple electrodes, for example, as described in copending U.S. application Ser. No. 11/683,981, titled "Implantable Cardiac Stimulation Device Providing Multi-Site Pacing and Method," filed Mar. 8, 2007, the entire disclosure of which is incorporated herein by reference. Further, although the foregoing description refers to epicardial electrodes, such an approach is equally applicable to endocardial electrodes.

The conduction-based approach described above may also be used in connection with a pacing device including multiple electrodes, one of which is designated for sensing only. In particular, the conduction-based approach described above may be applied to multiple electrodes placed for atrial pacing.

Figure 4:
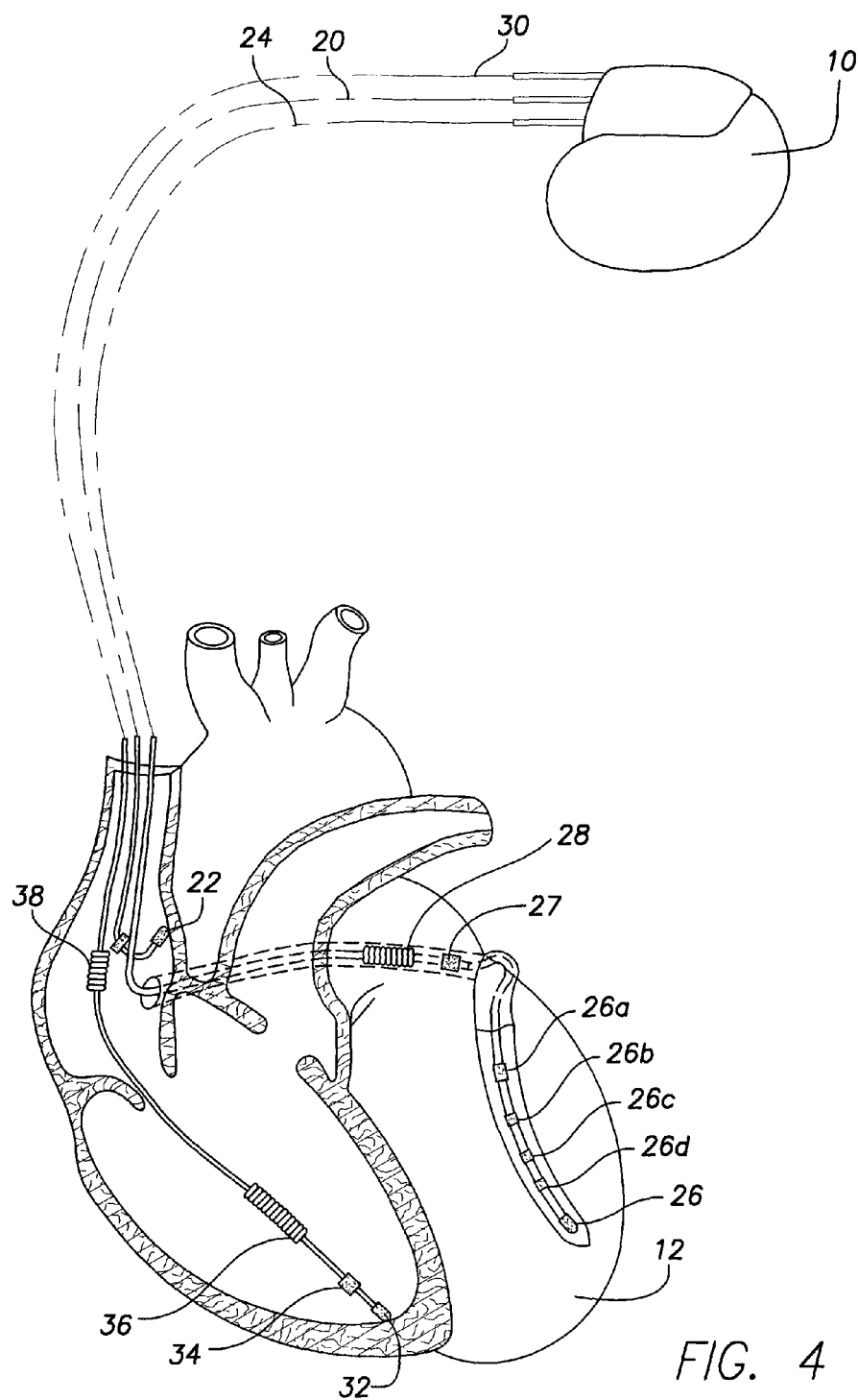
FIG. 4 illustrates a stimulation device in electrical communication with the patient's heart via three leads suitable for delivering multi-chamber stimulation and shock therapy.

FIG. 4 illustrates a stimulation device 10 in electrical communication with the patient's heart 12 via three transvenous leads 20, 24 and 30 suitable for delivering multi-chamber stimulation and shock therapy. To sense right atrial cardiac signals and to provide right atrial chamber stimulation therapy, the stimulation device 10 may be coupled to an implantable right atrial lead 20 including at least an atrial tip electrode 22, which typically is implanted in the patient's right atrial appendage.

To sense left atrial and/or left ventricular cardiac signals and to provide left-chamber pacing therapy, the stimulation device 10 may be coupled to a "coronary sinus" lead 24 configured to be placed in the "coronary sinus region" via the coronary sinus so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. It should be understood that the lead 24 could also be an epicardial lead placed at the time of thoracotomy or thoracoscopy.

Accordingly, the coronary sinus lead 24 may be configured to receive atrial and/or ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In addition to the left ventricular tip electrode 26, other left ventricle electrodes 26a, 26b, 26c, 26d may be included. For a more detailed description of an exemplary coronary sinus lead, refer to U.S. Pat. No. 5,466,254, titled "Coronary Sinus Lead with Atrial Sensing Capability" (Helland), the entire disclosures of which are incorporated herein by reference.

The stimulation device 10 is also shown in electrical communication with the patient's heart 12 via an implantable right ventricular lead 30 including, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 may be configured to receive cardiac signals, and deliver stimulation in the form of pacing and shock therapy to the right ventricle.

In one embodiment, the goal may be to identify, select and/or use one of the left ventricle electrodes 26a, 26b, 26c, 26d for pacing such that a fastest conduction across the cardiac tissue, specifically to the right ventricle, is achieved. In this case, any or all of the electrodes 32, 34, 36, 38 of the right ventricular lead 30 may be used as non-candidate electrodes to determine the activation time $\Delta T_{act}$ for each candidate electrode 26a, 26b, 26c, 26d.

As described above with respect to FIGS. 1-3, a pacing signal may be sent to each candidate electrode 26a, 26b, 26c, 26d in turn, and the last "activation" of the right ventricle electrodes 32, 34, 36, 38 may be sensed to determine the activation time $\Delta T_{act}$ for the particular candidate electrode.

Once the activation times $\Delta T_{act}$ for each of the candidate electrodes has been measured, a comparison may be made between the activation times $\Delta T_{act}$ of the candidates. Based on the comparison, one of the candidates may be identified as being preferred or optimal for pacing.

Although the foregoing description is in terms of single electrodes as candidates for pacing, it is understood that single electrodes and/or combinations of electrodes may be selected as candidates for pacing. For example, when four pacing electrodes 26a, 26b, 26c and 26d are available, up to ten possible combinations of electrode-pairing exist that may be evaluated as candidates for multiple-electrode pacing. These electrode-combinations include: 26a/26b, 26a/26c, 26a/26d, 26b/26c, 26b/26d, 26c/26d, 26a/26b/26c, 26a/26b/26d, 26a/26c/26d and 26b/26c/26d. Any or all of the combinations of electrode pairing may be evaluated, either with or without evaluation of single electrode candidates.

Alternatively or additionally, embodiments of the invention contemplate using an activation recovery interval (ARI)-based approach to identify, select and/or use an electrode or combination of electrodes for pacing. Such an approach may result in a reduced vulnerability to developing arrhythmia from electrotherapy, resulting in a safer application of electrotherapy.

Referring back to FIG. 1, in one embodiment, the goal may be to identify, select and/or use one of a plurality of electrodes 1, 2, 3, 4 or a combination of two or more of the electrodes 1, 2, 3, 4 for pacing such that a smallest ARI dispersion is achieved. Because ARI is related to the susceptibility of arrhythmia, minimizing ARI dispersion may reduce a vulnerability to developing arrhythmia.

Such an approach may selectively test individual candidates including one or more of the electrodes 1, 2, 3, 4 to determine an ARI for each candidate. The ARI for a particular candidate corresponds to the difference between the time of delivery of the pacing signal to cardiac tissue through the candidate electrode and the earliest end-of-recovery sensed from one or more of the other electrodes. The ARI for the candidate thus corresponds to the smallest ARI—of all measured ARIs—between the candidate electrode and the non-candidate electrodes.

Figure 5:
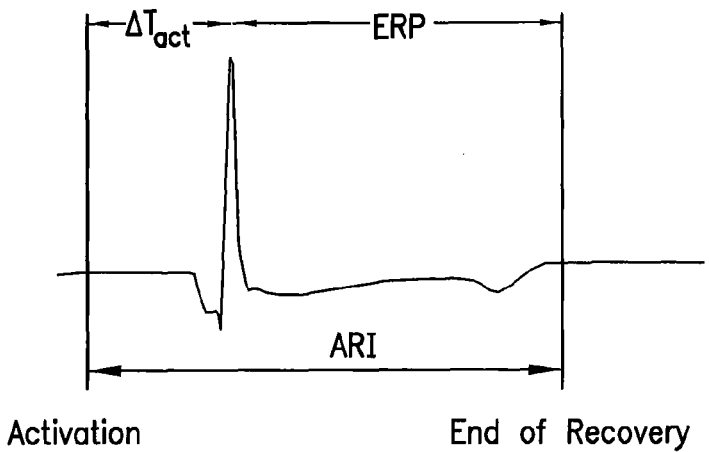
FIG. 5 illustrates a right ventricular intracardiac electrogram and its corresponding activation recovery interval (ARI) including an activation time $\Delta T_{act}$ and effective refractory period (ERP).

As shown in FIG. 5, ARI denotes a sum of activation time $\Delta T_{act}$ and effective refractory period (ERP). The activation time $\Delta T_{act}$ for each of the non-candidate electrodes may be determined as described above. The ERP for each of the non-candidate electrodes is determined as described below. Alternatively, the ARI may be measured directly, without measuring activation times and ERPs.

Regarding atrial electrodes, because the recovery phase for the atrium is usually hidden in the far-field R wave, detection of atrial cardiac activity and corresponding measurement of ERPs for atrial electrodes may be quite difficult. Thus, ERPs for atrial electrodes may be determined or measured beforehand, for example, during implant. Any suitable technique may be used to determine ERPs, whether known or hereafter developed, for example, such as described in "Methods for Determining the Refractory Period and Excitable Gap During Persistent Atrial Fibrillation in the Goat," M. Duytschaever et al., Circulation 2001; 104:957-962, which is incorporated by reference herein in its entirety. The ARI measurement for atrial non-candidate electrodes may thus be determined by measuring the activation time for the atrial non-candidate electrode and adding it to the predetermined ERP for that electrode.

Regarding ventricular electrodes, because the recovery phase for the ventricle is more prominent, as illustrated in FIG. 5, the ARI for a non-candidate ventricular electrode may be directly measured during testing of candidate electrodes. Thus, the ARI for non-candidate ventricular electrodes 1, 2, 3, 4 may be measured from the time a pacing stimulus is delivered to the candidate electrode and the end-of-recovery, e.g., end of the T wave, at the non-candidate electrode. In this case, the ARI for the non-candidate electrode corresponds to the time between activation at the candidate electrode and the end of recovery at the non-candidate electrode.

Further regarding ventricular electrodes, rather than directly measuring the ARI, the ERP and the activation time $\Delta T_{act}$ may be determined or measured for each non-candidate electrode. The activation time $\Delta T_{act}$ and the ERP may be determined using any suitable technique, whether known or hereafter developed, for example, such as described in connection with the electrophysical studies in "Novel Electrophysical Parameter of Dispersion of Atrial Repolarization Comparison of Different Atrial Pacing Methods," M. Ogawa, et. al., Journal of Cardiovascular Electrophysiology (February 2002); 13:110-117, which is incorporated by reference herein in its entirety. Activation recovery intervals may also be determined or measured as described in U.S. Pat. No. 7,107,093, the entire disclosure of which is incorporated herein by reference.

Once the ARI for each candidate electrode has been obtained, a comparison may be made between the ARIs of the candidates. Based on the comparison, one of the candidates may be identified as being preferred or optimal for pacing based on a smallest dispersion of ARI. Thus, the candidate electrode or electrode combination with the smallest ARI dispersion may be identified as the electrode or electrode combination to select and/or use for pacing.

It should be understood that the ARI dispersion may be measured in terms of standard deviation. Thus, the candidate electrode(s) with the smallest standard deviation of ARI may be identified as the electrode(s) to select and/or use for pacing.

Although the foregoing description is in terms of single electrodes as candidates for pacing, it should be understood that single electrodes and/or combinations of electrodes may be selected as candidates for pacing. The ARI-based approach described above may also be used in connection with a pacing device including multiple electrodes, one of which is designated for sensing only, as discussed above with respect to FIG. 4.

Embodiments of the invention also contemplate using a combined approach, i.e., using both activation times $\Delta T_{act}$ and ARI dispersions, to identify, select and/or use an electrode or combination of electrodes for pacing. Such an approach may desirably combine the results obtained by the conduction-based approach and the ARI-based approach individually. For example, such a combined approach may take into account both hemodynamics and arrhythmia susceptibility to identify a preferred or optimal pacing configuration.

Using only a conduction-based approach may identify an electrode or electrodes that, while providing desirable conduction and hemodynamics, yields a largest ARI dispersion among the candidate electrodes. Thus, while efficiency/performance of pacing using the identified electrode(s) may be desirable, the relatively large or increased likelihood of developing arrhythmia may be unacceptable. Using a combined approach may avoid such an undesirable result.

For a combined approach, the activation times $\Delta T_{act}$ and ARI dispersions may be obtained and compared as discussed above. The identification of the electrode(s) to be used for pacing may then be based on the results of both comparisons.

For example, the results from one or both comparisons may be weighted to allow the results from the different comparisons to be combined into a meaningful result and/or to create a particular preference, such as for better hemodynamics or for reduced susceptibility of arrhythmia. Such weighting factors may be determined empirically, and may be set based on a desired type of pacing. For example, better hemodynamics may be more important for cardiac resynchronization therapy (CRT) pacing, and thus the result of the conduction-based comparison may be more heavily weighted. For prevention-type pacing, reduced susceptibility of arrhythmia may be more important, and thus the result of the ARI dispersion comparison may be more heavily weighted.

It should be understood that the foregoing approaches may be applied to all types of pacing, including antitachycardia pacing (ATP).

Figure 6:
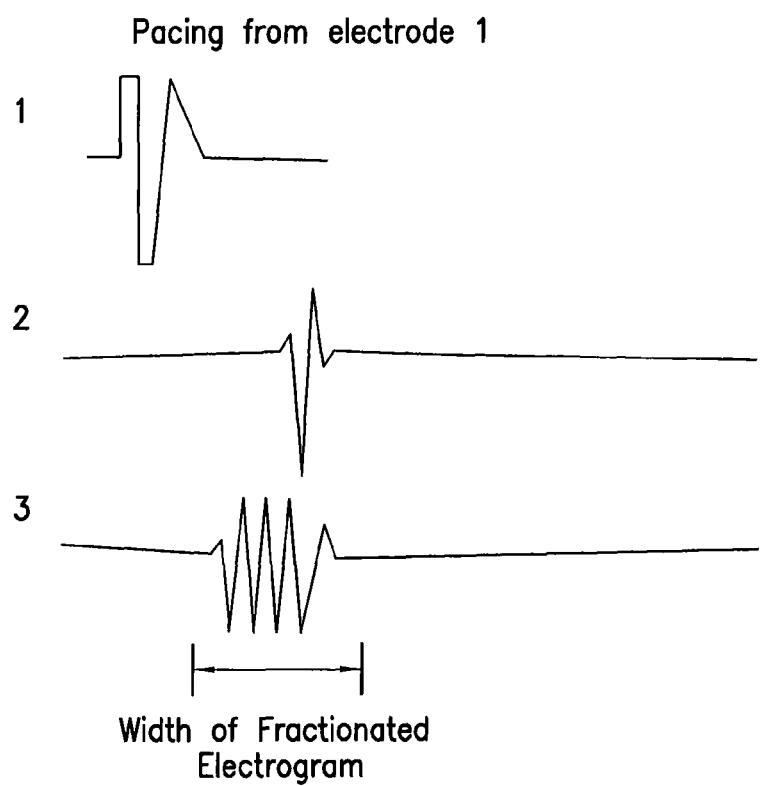
FIG. 6 illustrates a conduction pattern representing a pacing stimulus delivered from the first electrode of FIG. 1 and corresponding cardiac activation sensed at the second and third electrodes, wherein the cardiac activation at the third electrode is a fractionated electrogram having an overall width and peak-to-peak width features.

Alternatively or additionally to the approaches described above, an optimal electrode for pacing may be selected based on the presence of a fractionated electrogram. As illustrated in FIG. 6, a fractionated electrogram is a complex in which multiple small peaks exist. This may be due to non-uniform wave propagation, for example, across some sort of suboptimal conducting zone of cardiac tissue. Pacing electrodes or electrode combinations may be selected that do not lead to any fractionated electogram sensed at the other electrodes. If a fractionated electrogram is present for all available pacing configurations, the pacing electrode or electrode combination that leads to the smallest width of fractionated electogram may be selected. Further, for each non-candidate electrode, the peak-to-peak widths within a fractionated electrogram may be measured to obtain a standard deviation. The pacing electrode or electrode combination that leads to the smallest standard deviation may be selected.

Figure 7:
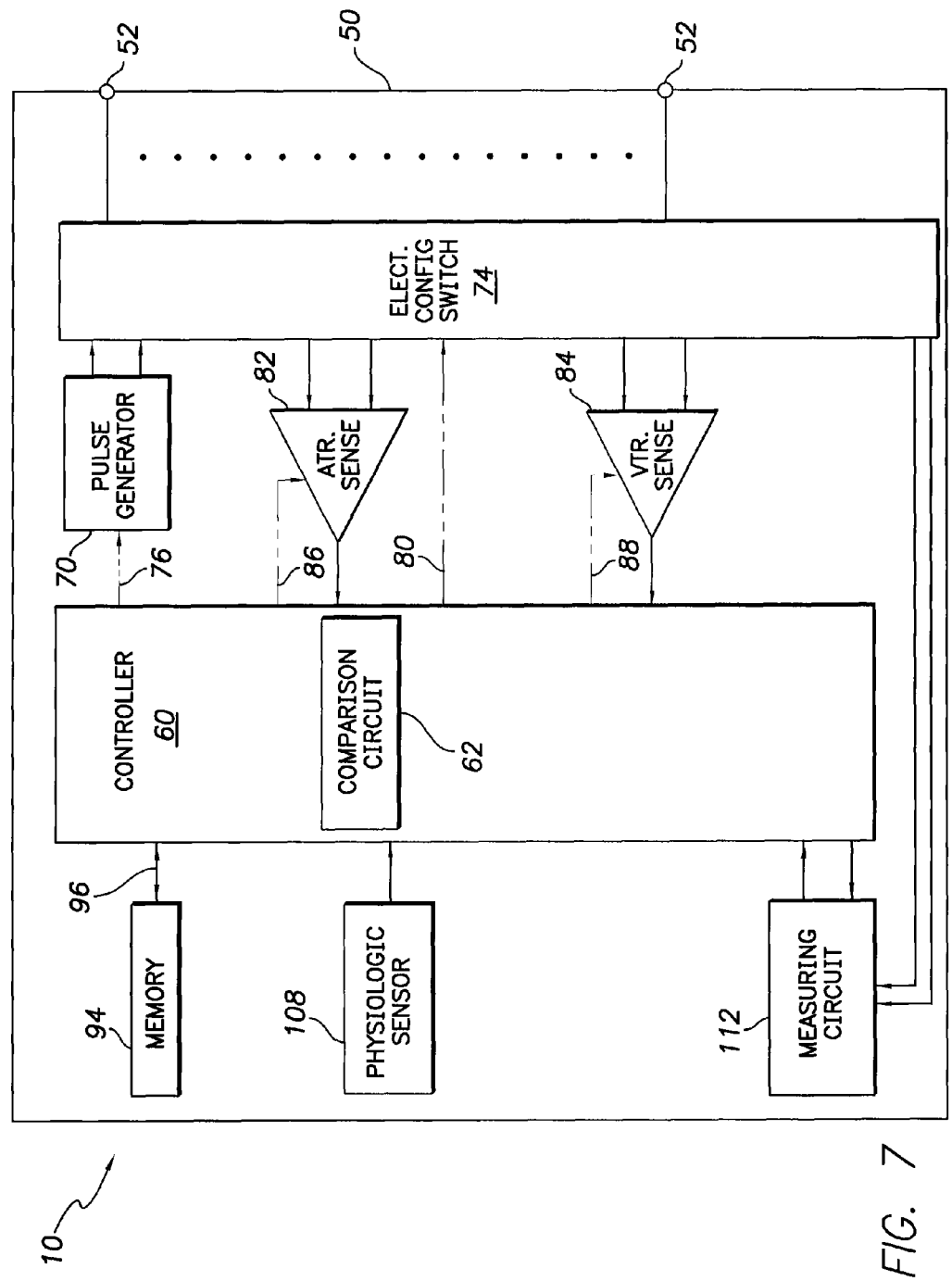
FIG. 7 illustrates a simplified block diagram of the implantable stimulation device, as illustrated in FIG. 4.

FIG. 7 illustrates an exemplary simplified block diagram of the implantable stimulation device 10, as illustrated in FIG. 4. While particular components are illustrated in FIG. 7, this is for illustration purposes only, and duplication, elimination or addition of components is possible to provide a device suitable to a particular treatment. Thus, only components relating to an understanding of the present invention are shown, without being limiting.

The stimulation device 10 includes a housing 50 which may be programmably selected to act as a return electrode for unipolar pacing and sensing electrode configurations. The housing 50 includes various terminals 52 for electrically connecting to various electrodes, such as shown in FIG. 4, associated with various stimulation sites within or on the heart 12. It is understood that the stimulation device 10 may include a multi-port connector capable of accommodating any combination of unipolar, bipolar or multipolar leads connecting to the various electrodes. The arrangement and type of leads and electrodes used may vary depending on the type of stimulation therapy to be delivered and individual patient need.

The stimulation device 10 includes a controller 60 that controls various modes of stimulation therapy and the identification of a preferred or optimum pacing configuration, as discussed herein. The details of the design and operation of the controller 60 are not critical to the present invention. Rather, any suitable controller 60 may be used that carries out the functions described herein.

The controller 60 includes a microprocessor, or equivalent control circuitry, configured to execute various functions and to control other elements in accordance with the desired operation of the device 10. The controller 60 may include logic and timing circuitry, state machine circuitry, I/O circuitry, and any other appropriate circuitry. The controller 60 is capable of processing and/or monitoring input signals (data) as controlled by a program code stored in a designated block of memory 94.

The controller 60 includes a comparison circuit 62 that is configured to carry out the comparisons of activation times $\Delta T_{act}$ and ARI dispersions as discussed herein. As discussed further below, data from the electrodes may be received by the controller 60, processed as desired and provided to the comparison circuit 62.

As shown in FIG. 7, a pulse generator 70 may be configured to generate pacing stimulation pulses for delivery by the leads to one or more desired electrodes. The pulse generator 70 is controlled by the controller 60 via appropriate control signals 76 to trigger the stimulation pulses. The pulses are delivered via a switch bank 74, which is controlled by the controller 60 via appropriate control signals 80. The switch bank 74 includes a plurality of switches for connecting the desired electrodes to the appropriate I/O circuits, thereby providing complete electrode programmability. Accordingly, the switch bank 74, in response to a control signal 80 from the controller 60, may determine the "pacing polarity" of electrode configurations (e.g., unipolar, bipolar, combined manner, etc.) used to deliver stimulation pulses and the "sensing polarity" of electrode configurations used to sense cardiac activity, by selectively closing the appropriate combination of switches (not shown).

An atrial sensing circuit 82 and a ventricular sensing circuit 84 are selectively coupled to the leads and electrodes, through the switch bank 74, for sensing the presence of cardiac activity. To sense events occurring within each chamber or at each stimulation site independently, the atrial and ventricular sensing circuits 82 and 84 may include dedicated independent sense amplifiers associated with each stimulation site within the heart 12. Each of the atrial sensing circuit 82 and the ventricular sensing circuit 84 may include a discriminator, which is a circuit that senses and can indicate or discriminate the origin of a cardiac signal.

The inputs to each sense amplifier 82, 84 may be programmable and may be selected, for example, by the controller 60, in any combination of available electrode terminals 52 to provide independent identification of inputs from the various electrodes. Unique sensing circuitry may be used for each electrode to allow discrimination of a detected event. Each of the atrial sensing circuit 82 or the ventricular sensing circuit 84 may employ one or more low power, precision amplifiers with programmable gain and/or automatic gain control, bandpass filtering, and a threshold detection circuit, to selectively sense the cardiac signal of interest. The sensing amplifiers 82, 84 receive control signals over signal lines 86, 88 from the controller 60 for the purposes of controlling the gain, threshold, polarization charge removal circuitry (not shown), and the timing of any block circuitry (not shown) coupled to the inputs of the sensing amplifiers, as is known in the art.

The outputs of the atrial and ventricular sensing circuits 82 and 84 may be connected to the controller 60 for triggering or inhibiting the atrial and ventricular pulse generators 70 and 72, respectively, as well as for providing data from the electrodes to determine a preferred or optimal pacing configuration in accordance with the present invention. Alternatively or additionally, data from the electrodes may be provided to the controller 60 by one or more physiologic sensors 108 suitably positioned on or in the heart, or by a suitable measuring circuit 112.

In carrying out the approaches described herein, the controller 60 selects a plurality of individual electrodes and/or electrode combinations as candidates for pacing. The controller 60 controls the pulse generator 70 to selectively output a pacing pulse to one of the candidate electrodes or candidate electrode combinations. The controller 60 also controls the inputs to one or more of the sensing circuits 82, 84, the physiologic sensor 108 and/or the measuring circuit 112 via the electrode configuration switch 74 to obtain various activation time $\Delta T_{act}$, ARI and/or fractionated electrogram measurements based on the activity sensed at one or more of non-candidate electrodes in response to the pacing pulse. The process of testing each candidate electrode or electrode combination may be repeated until all have been tested before the activation time $\Delta T_{act}$, ARI and/or fractionated electrogram data for the candidate electrode is sent to the comparison circuit 62 for analysis. Alternatively, the activation time $\Delta T_{act}$, ARI and/or fractionated electrogram data of successively tested candidates may be compared by the comparison circuit 62 to reduce the amount of data stored in the memory 94 for later comparison.

In either case, the comparison circuit 62 may compare the activation time $\Delta T_{act}$, ARI and/or fractionated electrogram data obtained from testing the candidate electrodes and/or electrode combinations, and provide the results to the controller 60. When the data of successively tested candidates is compared, the controller 60 may use each successive comparison result to methodically eliminate the less desirable candidate and finally identify an electrode or electrode combination for pacing. Otherwise, the controller 60 may simply use an overall result from the comparison circuit 62 to identify an electrode or electrode combination for pacing.

It should be understood that the controller 60 may perform one or more intermediate steps to support the various comparisons made by the comparison circuit 62. For example, when a combined conduction-based and ARI-based approach is used, the controller 60 may provide the weighting for comparison.

In general, the various components illustrated in FIG. 7 may be used to carry out a process of identifying a preferred or optimum pacing configuration. It should be understood, however, that other configurations of the implantable stimulation device 10 may be employed to carry out such a process.

Figure 8:
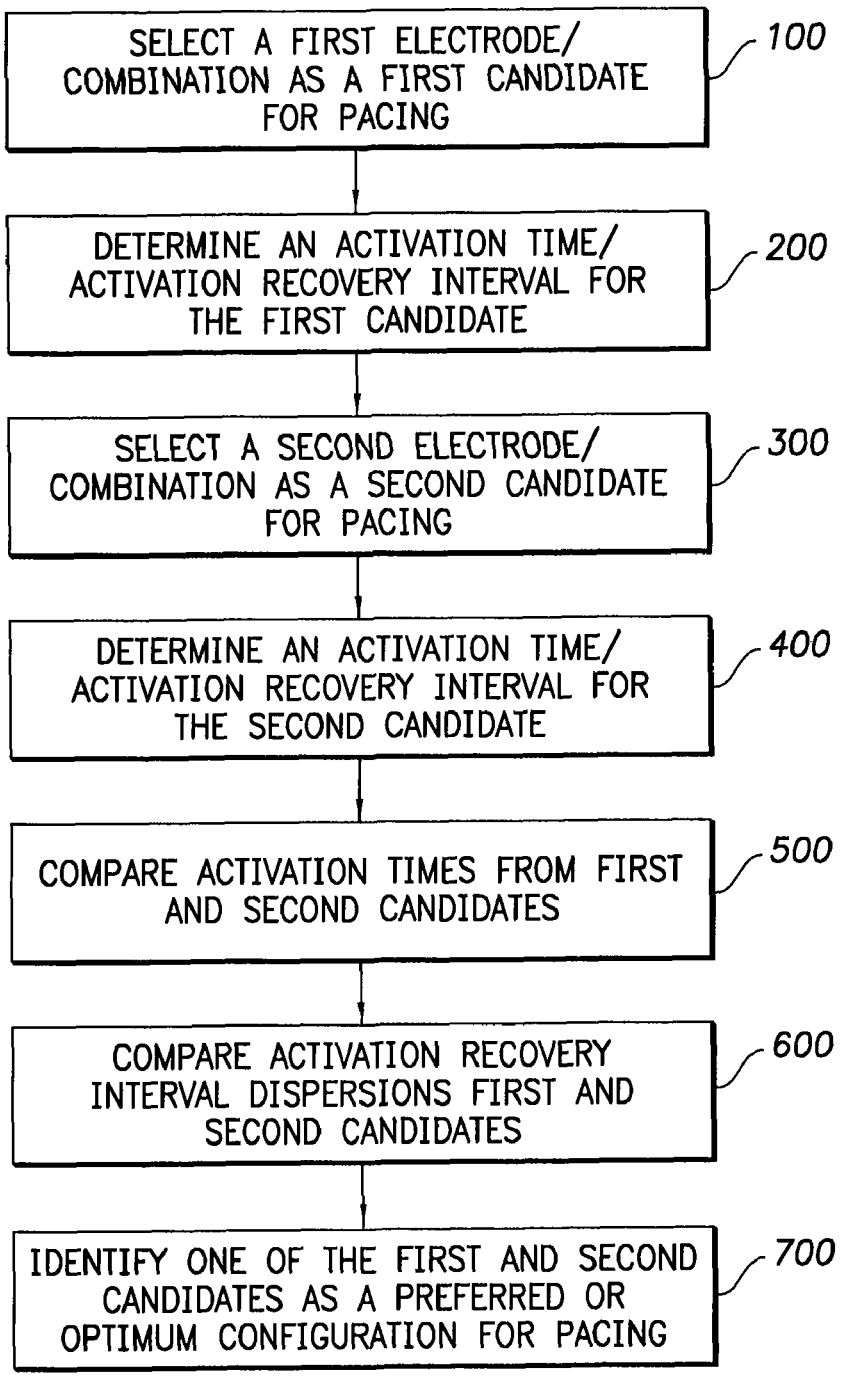
FIG. 8 is a flow chart related to identifying an optimum electrode pacing configuration.

With reference to FIG. 8, a process of identifying an electrode or electrode combination for pacing, from a number of candidate electrode and/or electrode combinations of a multi-electrode implantable cardiac electrotherapy device, may begin by selecting a first electrode or electrode combination as a first candidate to be used for pacing [block 100]. Next, a candidate activation time $\Delta T_{act}$ and/or a candidate ARI may be determined for the first candidate [block 200]. As discussed above, this process involves determining non-candidate activation times and ARIs by delivering a pacing pulse to cardiac tissue through the first candidate and measuring and comparing various cardiac-activity related measurements obtained through the non-candidate electrodes.

A second electrode or electrode combination may then be selected as a second candidate to be used for pacing [block 300]. Again, a candidate activation time $\Delta T_{act}$ and/or candidate ARI may be determined for the second candidate [block 400].

Next, the activation times $\Delta T_{act}$ for the first and second candidates may be compared [block 500]. Alternatively or additionally, the ARI for the first and second candidates may be compared [block 600]. Based on the comparisons, with or without an additional step of weighting as discussed above, one of the first and second candidates may be identified as a preferred or optimum configuration for pacing [block 700]. Once the process is complete, the identified electrode or electrode combination may be used to execute a pacing therapy as necessary or desired.

Although not shown for the sake of simplicity, it should be understood that suitable loops may be included in the illustrative flowchart of FIG. 8 to process three or more candidate electrodes or electrode combinations. Such a loop may occur before or after a comparison is made, as explained above with respect to FIG. 7.

Further, it should be understood that the foregoing methods may be used to periodically monitor and/or update optimal electrode selection. For example, the device may be configured to periodically monitor the electrode selection. Any suitable period may be used, such as monthly, weekly, etc. Alternatively, the device may be configured to continuously monitor the electrode selection.

In some embodiments, the device may implement one or more of the foregoing methods of selecting one or more electrodes for pacing upon detection of a preset cardiac parameter, for example. Alternatively or additionally, the device may periodically (e.g., monthly) implement one or more of the methods. In such a manner, the device may periodically "test" whether the current optimal pacing electrode may be replaced by another available electrode.

Although the present invention has been described with reference to preferred embodiments, persons skilled in the art will recognize that changes may be made in form and detail without departing from the spirit and scope of the invention.

What is claimed is:

1. A method of identifying an electrode or combination of electrodes of a multi-electrode implantable cardiac electrotherapy device for pacing, said method comprising:
   selecting a first electrode or combination of electrodes as a first candidate to be used for pacing;
   determining measurements comprising activation time $\Delta T_{act}$ and activation recovery interval (ARI) based on sensed cardiac electrical activity, for the first candidate;
   selecting a second electrode or combination of electrodes as a second candidate to be used for pacing;
   determining measurements comprising activation time $\Delta T_{act}$ and activation recovery interval (ARI) based on sensed cardiac electrical activity, for the second candidate;
   comparing the measurements for the first and second candidates; and
   identifying one of the first and second candidates for pacing based on the comparisons by identifying the candidate with at least one of a shortest activation time $\Delta T_{act}$ and a smallest ARI.

2. The method of claim 1 wherein identifying one of the first and second candidates for pacing is further based on a desired type of pacing.

3. The method of claim 1 wherein determining an activation time $\Delta T_{act}$ for either of the first and second candidates comprises:
   delivering a pacing pulse to the candidate;
   for each of a plurality of non-candidate electrodes:
      sensing cardiac activity at the non-candidate electrode;
      measuring the time between the delivery of the pacing pulse to the candidate and the sensing of cardiac activity at the non-candidate electrode;
   comparing the measured times; and
   selecting the largest measured time as the activation time $\Delta T_{act}$ for the candidate electrode.

4. The method of claim 1 wherein determining the ARI for either of the first and second candidates comprises:
   delivering a pacing pulse to the candidate;
   for each of a plurality of non-candidate electrodes positioned in or on a ventricle:
      sensing cardiac activity at the non-candidate electrode;
      measuring the time between the delivery of the pacing pulse to the candidate and the end of recovery of the sensed cardiac activity at the non-candidate electrode;
   for each of a plurality of non-candidate electrodes positioned in or on an atria:
      sensing cardiac activity at the non-candidate electrode;
      determining the time between the delivery of the pacing pulse to the candidate and the sensing of cardiac activity at the non-candidate electrode;
      summing the determined time and a predetermined effective refractory period corresponding to the non-candidate electrode,
   comparing the measured and summed times to each other; and
   selecting the smallest of the measured and summed times as the ARI for the candidate electrode.

5. A method of identifying an electrode or combination of electrodes of a multi-electrode implantable cardiac electrotherapy device for pacing, said method comprising:
   selecting a first electrode or combination of electrodes as a first candidate to be used for pacing based on a desired pacing type;
   determining measurements comprising activation time $\Delta T_{act}$ and activation recovery interval (ARI) based on sensed cardiac electrical activity, for the first candidate;
   selecting a second electrode or combination of electrodes as a second candidate to be used for pacing based on the desired pacing type;
   determining measurements comprising activation time $\Delta T_{act}$ and activation recovery interval (ARI) based on sensed cardiac electrical activity, for the second candidate;
   weighting a result of at least one of the comparison of the activation times $\Delta T_{act}$ and the comparison of the ARIs based on the desired type of pacing;
   comparing the measurements for the first and second candidates; and identifying one of the first and second candidates for pacing based on the comparison.

6. The method of claim 5 wherein:
when the desired type of pacing is cardiac resynchronization therapy, the activation times $\Delta T_{act}$ result is weighted more heavily than the ARI result; and
when the desired type of pacing is prevention type pacing, the ARI result is weighted more heavily than the activation times $\Delta T_{act}$ result.

* * * * *